(12) United States Patent
Brandl

(10) Patent No.: US 11,912,444 B2
(45) Date of Patent: Feb. 27, 2024

(54) PROCESS FOR THE CONDITIONED PACKAGING OF HARD GELATIN CAPSULES

(71) Applicant: AMCOR FLEXIBLES SINGEN GMBH, Singen (DE)

(72) Inventor: Oliver Brandl, Constance (DE)

(73) Assignee: AMCOR FLEXIBLES SINGEN GMBH, Singen (DE)

( * ) Notice: Subject to any disclaimer, the term of this patent is extended or adjusted under 35 U.S.C. 154(b) by 297 days.

(21) Appl. No.: 17/613,312

(22) PCT Filed: Jun. 3, 2020

(86) PCT No.: PCT/EP2020/065277
§ 371 (c)(1),
(2) Date: Nov. 22, 2021

(87) PCT Pub. No.: WO2020/245147
PCT Pub. Date: Dec. 10, 2020

(65) Prior Publication Data
US 2022/0227507 A1 Jul. 21, 2022

(30) Foreign Application Priority Data
Jun. 3, 2019 (EP) ..................................... 19177985

(51) Int. Cl.
*B65B 11/52* (2006.01)
*A61J 1/03* (2023.01)
(Continued)

(52) U.S. Cl.
CPC ............... *B65B 11/52* (2013.01); *A61J 1/035* (2013.01); *A61K 9/4816* (2013.01);
(Continued)

(58) Field of Classification Search
CPC ......... B65B 11/52; B32B 15/08; B65D 73/00; B65D 85/42; B65D 75/327; B65D 81/266
(Continued)

(56) References Cited

U.S. PATENT DOCUMENTS

2003/0235664 A1 12/2003 Merical et al.
2007/0104655 A1* 5/2007 Zierenberg ............. A61K 9/008
128/200.23
(Continued)

FOREIGN PATENT DOCUMENTS

CN 102438825 A 5/2012
CN 102973571 A 3/2013
(Continued)

OTHER PUBLICATIONS

PCT International Search Report, International Application No. PCT/EP2020/065277, dated Aug. 25, 2020, 4 pages.

*Primary Examiner* — Jacob A Smith

(57) ABSTRACT

A method for conditioning a hard gelatin capsule (50) having any moisture content to a dry and non-brittle state when packed for at least one week in a cavity (45) of a blister base (40) closed by a lid film (35) comprising an aluminium foil, wherein the hard gelatin capsule (50) is a hard starch capsule manufactured from collagen and the hard gelatin capsule (50) contains pharmaceuticals and wherein the dry state of the hard gelatin capsule (50) means a relative humidity of less than 50% at room temperature and the non-brittle state means that the hard gelatin capsule (50) does not break when pressed out of the cavity (45) of the blister base (40) through the lid film (35). The lid film (35) and/or the blister base (40) comprise/s a moisture-regulating buffer layer (20) with a predefined humidity. The moisture-regulating buffer layer (20) consists of a polymer or polymer mixture containing 1 to 60 wt. % of an absorber material which is either a hygroscopic salt, a silica gel or a zeolite or
(Continued)

a mixture of any of said absorber materials, wherein the absorber material buffers the humidity in the space within the cavity (45) surrounding the hard gelatin capsule (50) to lie in a range between 10 and 50% r.h.

12 Claims, 4 Drawing Sheets

(51) Int. Cl.
*A61K 9/48* (2006.01)
*B65D 75/32* (2006.01)
*B65D 81/26* (2006.01)

(52) U.S. Cl.
CPC .......... *A61K 9/4825* (2013.01); *B65D 75/327* (2013.01); *B65D 81/266* (2013.01)

(58) Field of Classification Search
USPC ............................ 53/400; 206/204, 438, 484
See application file for complete search history.

(56) References Cited

U.S. PATENT DOCUMENTS

| | | | |
|---|---|---|---|
| 2007/0160789 A1* | 7/2007 | Merical | .................. B32B 15/08 |
| | | | 206/204 |
| 2010/0100093 A1 | 4/2010 | Azure | |

FOREIGN PATENT DOCUMENTS

| | | | | |
|---|---|---|---|---|
| CN | 104169187 A | 11/2014 | | |
| CN | 105189110 A | 12/2015 | | |
| CN | 106414846 A | 2/2017 | | |
| CN | 107735251 A | 2/2018 | | |
| CN | 109330988 A | 2/2019 | | |
| EP | 1733872 A1 | 12/2006 | | |
| EP | 2478886 A1 * | 7/2012 | ............. | B32B 15/08 |
| EP | 2478886 A1 | 7/2012 | | |
| WO | 2006115264 A1 | 11/2006 | | |
| WO | 2008041663 A1 | 4/2008 | | |

* cited by examiner

PROCESS FOR THE CONDITIONED PACKAGING OF HARD GELATIN CAPSULES

The invention relates to a method for conditioning a hard gelatin capsule having any moisture content to a dry and non-brittle state when packed in a cavity of a blister base closed by a lid film, wherein the hard gelatin capsule is a hard starch capsule manufactured from collagen and the hard gelatin capsule contains pharmaceuticals and wherein the dry state of the hard gelatin capsule means a relative humidity of less than 50% at room temperature and the non-brittle state means that the hard gelatin capsule does not break when pressed out of the cavity of the blister base through the lid film.

Hard gelatin capsules are considered one of the most commonly used dosage forms in pharmaceutical drugs delivery because of their ease in swallowing, the shells have no taste and the drugs which are not having a pleasant taste and smell can be administered easily. They can be manufactured in different colours and the drug will be released easily as there is no compaction. Hard gelatin capsules are not generally used for compounds that are highly soluble because the drug is delivered at once. Materials and packaging materials which release water cause softening of the capsules. Substances that absorb water cause brittleness of the powder and the capsule. That means the packaging for this kind of materials is critical for the correct drug delivery.

EP-A-2478886 discloses a packaging material for the production of a packaging for moisture-sensitive products. Said packaging material provides in a head space of the packaging above the products a relative humidity (RH) of 5 to 80% at a temperature of −20° C. to 50° C. Said packaging material comprises an aluminium foil as a water vapour barrier, wherein the aluminium foil comprises on a first side a moisture-regulating absorber layer and on the second side is uncoated, coated, painted or laminated, wherein the moisture-regulating absorber layer contains 0.15 to 95% by weight of a hygroscopic salt and/or 0.15 to 95% by weight of silica gel and/or 0.15 to 95% by weight of zeolites.

EP-61-2135738 describes a method for setting the moisture level of a moisture-absorbing material in a laminate for manufacturing blister base parts of blister packs for packaging moisture-sensitive products. Said laminate comprises a barrier layer against water vapour and gases, an outer layer made of a polyamide arranged on a first side of the barrier layer, a moisture-absorbing material arranged on the second side of the barrier layer, and a sealable inner layer made of a polyolefin arranged on the second side of the barrier layer and covering the absorbing material. In order to absorb water in the polyamide outer layer, the laminate is passed through a water bath or wetted or vaporised with water and subsequently rolled up for storage, wherein the water absorbed by the polyamide outer layer is released into the absorber material in the rolled-up laminate by permeation via the inner layer made of polyolefin.

US-A1-2007/160789 describes a film structure and a method of manufacturing and use of said film structure having a desiccant material within a film layer of the film structure wherein said film structure is utilized in a package for a product that is sensitive to the presence of moisture such as a drug coated medical stent or device.

EP-A1-2068812 discloses a medicinal package comprising a chemical absorption-type desiccant such as metallic oxide for reducing smells in a medicinal preparation.

EP-A1-1733872 discloses a cold formable laminate for the production of blisters for packaging products sensitive to moisture, oxygen and acid, wherein the laminate comprises a barrier layer as a barrier against water vapour and gases, a plastic layer arranged on a first side of the barrier layer as an outer layer and a sealable inner layer arranged on the second side of the barrier layer, wherein a moisture, oxygen and acid absorbing absorber material is arranged on the second side of the barrier layer.

The aim of this invention is to provide a method for packaging a hard gelatin capsule in a blister package in a dry and non-brittle state that avoids the risk of brittle failure when the hard gelatin capsule is pressed out of the cavity through the lid film of the blister package.

Present invention provides a method for conditioning a hard gelatin capsule having any moisture content to a dry and non-brittle state when packed in a cavity of a blister base closed by a lid film, wherein the hard gelatin capsule is a hard starch capsule manufactured from collagen and the hard gelatin capsule contains pharmaceuticals and wherein the dry state of the hard gelatin capsule means a relative humidity of less than 50% at room temperature and the non-brittle state means that the hard gelatin capsule does not break when pressed out of the cavity of the blister base through the lid film, wherein the method includes the following process steps (a) to (c):

a) providing a lid film comprising an aluminium foil (15) and if applicable a sealing layer made of a polyethylene and/or a moisture regulating buffer layer, further providing a blister base having at least one cavity, the lid film and/or the blister base comprising a moisture regulating buffer layer with a predefined humidity, wherein the moisture-regulating buffer layer consist of a polymer or polymer mixture containing 1 to 60 wt % of an absorber material which is either a hygroscopic salt, a silica gel or a zeolite or a mixture of any of said absorber materials, wherein the moisture-regulating buffer layer (20), the lid film and/or the blister base comprising the buffer layer or a prelaminate for the lid film and/or the blister base comprising the buffer layer is exposed to a predefined moisture level, wherein the predefined moisture level of the buffer layer is such that it buffers the humidity in the space surrounding the hard gelatin capsule within the cavity closed by the lid film to lie in a range between 10 and 50% r.h.;

b) placing the hard gelatin capsule in a cavity of the blister base provided in step (a) and closing the cavity by laminating the lid film provided in step (a) to the blister base comprising the hard gelatin capsule;

c) Storing the gelatin capsule for at least a week in the cavity closed by the lid film.

Further preferred embodiments of the inventive method are described in the claims directly or indirectly depending on claim 1.

In present text, the relative humidity sometimes is abbreviated by r.h.

The hard gelatin capsule may have any moisture content when introduced into the cavity of the blister base before closing the cavity by sealing the lid film onto the blister base. Preferably the moisture content of the hard gelatin capsule enclosing the pharmaceutical is in the range of between 5 to 90% r.h.

In order to get a moisture regulating buffer layer having a predefined humidity, the moisture-regulating buffer layer has to be moistened to that value, i.e. for the absorber material to have a buffering function at a predefined humidity level to be set, it must be moistened to this value.

The lid film consists preferably of a 10-30 µm thick hard aluminium foil and an inner layer, i.e. a layer directed to the blister base, made of polyethylene having a mass per unit area of 10-50 g/m² and as the case may be of a moisture-regulating buffer layer that is bonded to the aluminium foil using or not using an adhesion promotor or a sealing layer.

The absorber materials are suitable for adjusting a predefined relative humidity in the cavity of a blister base that is closed by a lid film. Therefore, the moisture-regulating buffer layer preferably is exposed to a predefined moisture level before or after lamination with one or more other layers of the lid film and/or the blister base. The humidity of the moisture-regulating buffer layer comprising the absorber material can be preset by moistening the moisture-regulating buffer layer either before or after laminating it to other layers of the laminate of the lid film and/or the blister base. The moistening can be done by passing the laminate comprising the moisture-regulating buffer layer through a water bath, splashing the moisture-regulating buffer layer with water, or storing and/or processing the moisture-regulating buffer layer in an atmosphere having a predefined relative humidity.

Preferred hygroscopic salts having a high solubility in water are e.g. $CaCl_2 \cdot 6H_2O$, $Ca(NO_3)_2 \cdot 4H_2O$, $Na_2CO_3 \cdot H_2O$, NaCl, $NaNO_3$, $Na_2SO_4$, $Na_2SO_4 \cdot 10H_2O$, $MgSO_4 \cdot 7H_2O$, $Na_2CO_3 \cdot 10H_2O$, $KNO_3$ or $CH_3COOK$.

Especially preferred is $CH_3COOK$ (potassium acetate) as absorber material in the moisture-regulating buffer layer. Potassium acetate, also called KAc, has a very high solubility in water.

The moisture-regulating buffer layer as humidity absorber layer contains preferably 2 to 20% by weight of the absorber material.

In a preferred embodiment of the inventive method, the lid film and/or the blister base comprise/s an innermost sealing layer directed to the cavity, wherein the sealing layer is made of a polyethylene (PE), or another polyolefin, or modified polyolefins, or a cyclo-olefin copolymer (COC), or a ionomer. Particularly preferred as sealing layer is a mixture of a low density polyethylene (LDPE) and a high density polyethylene (HDPE). The innermost sealing layer is a layer that lies between the lidding film and the blister base, but is either part of the lid film or the blister base.

The lid film and/or the blister base consist/s preferably of a laminate comprising an aluminium foil as a moisture barrier.

In a preferred method, a lid film is used that comprises a moisture-regulating buffer layer between an aluminium foil and a sealing layer, wherein the moisture-regulating buffer layer is optionally bonded to the aluminium foil by means of an adhesion promoter layer.

In a further preferred method, the blister base comprises an aluminium foil and on its inner side directed towards the cavity a moisture-regulating buffer layer, wherein the moisture-regulating buffer layer is optionally bonded to the aluminium foil by means of an adhesion promoter layer.

The optional adhesion promoter layer lying between the aluminium foil and the moisture-regulating buffer layer consists preferably of an ethylene-acrylic acid copolymer (EAA), or an ethylene-methacrylate copolymer (EMA), or a polypropylene (MAH-PP) grafted with maleic anhydride, or a polyurethane (PU) adhesive or an adhesive layer produced with solvent-containing or solvent-free adhesives.

The moisture-regulating buffer layer of the blister base and/or the lid film is preferably made of polyethylene (PE), polypropylene (PP), ethylene-acrylic acid copolymer (EAA), ethylene-methacrylate copolymer (EMA), polyethylene terephthalate (PET), polyvinyl chloride (PVC) or mixtures of any of the aforementioned polymers, wherein the polymer or polymer mixture contains 1 to 60% by weight of the absorber material.

The blister base may comprise on the outer side of the aluminium foil a film made of oriented polyamide (OPA) as outermost base layer of the blister package. An adhesion layer may be arranged between said OPA-layer and the aluminium foil.

A blister base having from the inside directed to the cavity to the outside the layer sequence containing a sealing layer, a moisture-regulating buffer layer, an adhesion promotor layer, an aluminium foil, an adhesive layer and a OPA-layer may be produced by first producing a prelaminate comprising the OPA-film and the aluminium foil using an intermediate adhesive layer. Subsequently, the adhesion promoter layer, the moisture-regulating buffer layer with the absorber material, preferably potassium acetate particles, and the sealing layer may be coextruded onto the aluminium side of the prelaminate.

Tests:

Three types of capsules are packaged in a blister package (blister type 1) having a blister base part consisting of a barrier layer made of a 45 μm thick aluminium foil, whose outer surface is covered with a 25 μm thick layer of OPA, wherein the inner surface of the aluminium foil, i.e. the surface directed to the cavity, is covered with an absorber layer made of PE comprising 50 g/m² CaO. Said blister package dries the cavity and the hard gelatin capsule down to <10% r.h. The lid film used for closing the cavities of this blister base part is made of a 20 μm thick hard aluminium foil and an inner layer of PE having a mass per unit area of 15 g/m².

Three types of capsules are packaged in a blister package (blister type 2) having a blister base part consisting of a barrier layer made of a 45 μm thick aluminium foil, whose outer surface is covered with a 25 μm thick layer of OPA and its inner surface is covered with a 60 μm thick layer of PVC. Blister 2 does not comprise any humidity absorber component. The lid film used for closing the cavities of this blister base part is made of a 20 μm thick hard aluminium foil and an inner heat sealing layer having a mass per unit area of 7 g/m².

A further blister package (blister type 3) has a blister base part consisting of a barrier layer made of a 60 μm thick aluminium foil, whose outer surface is covered with a 25 μm thick layer of OPA, wherein the inner layer directed against the cavity is covered by a 40 μm thick layer made of HDPE. Said layers have a different functionality: the OPA layer improves the formability of the cavity, Al is the barrier against diffusion of humidity and HDPE improves the stiffness of the blister base. Blister 3 does not comprise any humidity absorber component. The lid film used for closing the cavities of this blister base part is made of a 20 μm thick hard aluminium foil and an inner heat sealing layer having a mass per unit area of 7 g/m².

Hard gelatin capsules have also been packaged in a blister package (blister type 4) having a blister base part consisting of a barrier layer made of a 70 μm thick aluminium foil, whose outer surface is covered with a 25 μm thick layer of OPA, wherein the inner surface of the aluminium foil, i.e. the surface directed to the cavity, is covered with a moisture-regulating buffer layer made of PE comprising 50 g/m² KAc.

A further embodiment of a blister package (blister type 5) containing KAc as absorber agent has been used containing a barrier layer made of a 45 μm thick aluminium foil, whose outer surface is covered with a 25 μm thick layer of OPA, wherein the inner surface of the aluminium foil, is covered with a 23 µm thick layer of PET and a subsequent innermost moisture-regulating buffer layer made of PE comprising 50 g/m² KAc.

A further embodiment of a blister package (blister type 6) containing KAc as absorber agent has been used containing a barrier layer made of a 45 µm thick aluminium foil, whose outer surface is covered with a 25 µm thick layer of OPA and an outermost layer of 60 µm thick PVC, wherein the inner surface of the aluminium foil is covered with a moisture-regulating buffer layer made of PE comprising 50 g/m² KAc.

The lid film used for closing the cavities of this blister base parts (blister type 4 to 6) is made of a 20 µm thick hard aluminium foil and an inner layer of PE having a mass per unit area of 15 g/m².

Said blister packages containing KAc as absorber agent dry the cavities and the hard gelatin capsules down to approximately 22% r.h.

The tested capsules are as follows:
Capsule S: Yellow softgel capsules containing fishoil having a size 00;
Capsule H: White/blue hard gelatin capsules having a size 00, which are empty;
Capsule V: White HPMC capsules having a size 00, which are empty.

Softgel capsules (capsule S) are single-piece gelatin capsules and are primarily used for oils and for active ingredients that are dissolved or suspended in oil. Softgel capsules are composed of gelatin manufactured from the collagen of animal skin or bone. Softgel capsules are often used as a delivery system for oral drugs, especially poorly soluble drugs. This is because the fill can contain liquid ingredients that help increase solubility or permeability of the drug across the membranes in the body. Liquid ingredients are difficult to include in any other solid dosage form such as a tablet.

The hard gelatin capsules (capsule H) are two-piece telescoping, hard starch capsules and are manufactured from collagen of animal skin or bone. The powder or spheroids inside of the capsule contains the active ingredient(s) and any excipients. Hard gelatin capsules are hard-shelled capsules which are made in two halves: e.g. a smaller-diameter "body" that is filled and then sealed using a larger-diameter "cap". Hard gelatin capsules usually contain dry, powdered ingredients or miniature pellets. The typical moisture content of hard gelatin capsules is 13-16% r.h. of the shell, at temperature of 15-25° C. and a maximum of 70% r.h. The hard gelatin capsules have a size 00, have a volume of 0.7 ml, a length of 21.3 mm and an external diameter of 7.3 mm.

Two-piece capsules have been used for almost a century in the pharmaceutical field, and gelatin has been adopted as the main material of these capsules due to its excellent characteristic as a gelatinizer. The gelatin dissolves under high concentration into water of a high temperature and quickly gels at room temperature. The thickness of the film made by the gelatin becomes uniform. However, gelatin is one of the proteins derived from animals. Several materials have been examined as a substitute for the gelatin in two-piece hard capsules. Hydroxypropylmethyl cellulose (HPMC) has become a alternative material for two-piece capsules.

The HPMC capsules (capsule V) are vegetable capsules and are composed of HPMC (Hydroxypropylmethylcellulose). HPMC capsules have a low moisture content level (5-6% at 50% R.H), and will not retain elevated moisture levels after exposure to highly humid conditions. The HPMC capsules have a size 00, have a volume of 0.9 ml, a length of 23.3 mm and an external diameter of 8.2 mm.

The capsules used for the following tests were empty and came from the supplier Kapselwelt and had the following specifications:

| Hard gelatin capsules | |
|---|---|
| Size | 00 |
| Dimension | 21.3 × 7.3 mm |
| Volume | 0.7 ml |
| Filling quantity | 350-700 mg |
| Expires | August 2018 |
| Certificate number | Ca-C13000293240 |
| Order number | 1231 |

| HPMC | |
|---|---|
| Size | 00 |
| Dimension | 23.3 × 8.2 mm |
| Volume | 0.9 ml |
| Filling quantity | 480-950 mg |
| Expires | August 2020 |
| Certificate number | EK-X409038 |
| Order number | 2051 |

A test method was developed to demonstrate that some hard gelatin capsules are eventually breaking under dry conditions. It is supposed to show the risks in the push through application, when gelatin capsules, primarily packaged in a blister package (blister type 1) having a blister base part comprising an absorber layer made of PE with 50 g/m² CaO, a laminate which reduces the relative humidity below 10% r.h., get brittle so that they might break when pushing them through. The test objective is to find out the most suitable method that shows the highest fractured capsules percentage when packaged in said blister base part comprising the absorber layer made of PE with 50 g/m² CaO. The experiment was done by a tensile testing machine manufactured by Hegewald & Peschke.

Six blisters of different categories were stored in a climatic chamber at the condition 40° C./90% r.h. (temperature/relative humidity) for 1 week. The blisters were introduced to a tensile testing machine to find out the optimal test parameters regarding speed and position that result in the highest hard gelatin capsule fracture percentage.

Two push positions (middle or edge) are used by changing the blister position in the push through testing device manually.

Six blisters with six cavities are filled with empty capsules for some blister/capsule combinations. The tests are done at a relative humidity between 30 and 50% r.h. at a room temperature of 23° C.

The following results show that 0% breaking of HPMC capsules (capsule V) happens when packaged in both packaging materials, namely in blister type 1 and blister type 3. Moreover, the results show that 33% of hard gelatin capsules H are fractured when packaged in blister type 1 using highest speed 800 mm/min and middle position. At the same setting, no fracture of hard gelatin capsules happens when packaged in blister type 3 not having any humidity absorber material.

TABLE 1.1

Blister type 1 with capsules V

| Blister | Position | Speed mm/min | Fractured —/6 | Fractured (%) |
|---|---|---|---|---|
| 1 | Middle | 800 | 0 | 0 |
| 2 | Middle | 450 | 0 | 0 |
| 3 | Middle | 50 | 0 | 0 |
| 4 | Edge | 800 | 0 | 0 |
| 5 | Edge | 450 | 0 | 0 |
| 6 | Edge | 50 | 0 | 0 |

TABLE 1.2

Blister type 1 with capsules H

| Blister | Position | Speed mm/min | Fractured —/6 | Fractured (%) |
|---|---|---|---|---|
| 1 | Middle | 800 | 2 | 33 |
| 2 | Middle | 450 | 0 | 0 |
| 3 | Middle | 50 | 1 | 17 |
| 4 | Edge | 800 | 0 | 0 |
| 5 | Edge | 450 | 1 | 17 |
| 6 | Edge | 50 | 0 | 0 |

TABLE 1.3

Blister type 3 with capsules V

| Blister | Position | Speed mm/min | Fractured —/6 | Fractured (%) |
|---|---|---|---|---|
| 1 | Middle | 800 | 0 | 0 |
| 2 | Middle | 450 | 0 | 0 |
| 3 | Middle | 50 | 0 | 0 |
| 4 | Edge | 800 | 0 | 0 |
| 5 | Edge | 450 | 0 | 0 |
| 6 | Edge | 50 | 0 | 0 |

TABLE 1.4

Blister type 3 with capsules H

| Blister | Position | Speed mm/min | Fractured —/6 | Fractured (%) |
|---|---|---|---|---|
| 1 | Middle | 800 | 0 | 0 |
| 2 | Middle | 450 | 0 | 0 |
| 3 | Middle | 50 | 0 | 0 |
| 4 | Edge | 800 | 0 | 0 |
| 5 | Edge | 450 | 0 | 0 |
| 6 | Edge | 50 | 0 | 0 |

The above tables show that the highest fractured capsules H percentage results at a speed of 800 mm/min and at a middle position.

These optimal test parameters of a push speed of 800 mm/min and at a middle push position are used for further tests at different storage times, under the same storage conditions at 40° C. and 90% r.h. One objective is to find out if storage time affects the test results regarding the capsule breaking behaviour. The other is to find out statistically significant differences in the fracture behaviours of the capsules in the different packaging materials in blister type 1 comprising CaO as humidity absorber material and blister type 3 not containing any humidity absorber material. Ten blisters are tested by a tensile testing machine with the optimal test parameters for each aforementioned blister/capsule combination.

Test results after one week storage at 40° C. and 90% r.h.:

TABLE 2.1

Blister type 1 with capsules H

| Blister | Position | Speed mm/min | Fractured —/6 * | Description * |
|---|---|---|---|---|
| 1 | middle | 800 | 0 | Brittle |
| 2 | middle | 800 | 1 | Fractured |
| 3 | middle | 800 | 1 | Fractured |
| 4 | middle | 800 | 1 | Fractured |
| 5 | middle | 800 | 3 | Fractured |
| 6 | middle | 800 | 1 | Fractured |
| 7 | middle | 800 | 0 | Brittle |
| 8 | middle | 800 | 3 | Fractured |
| 9 | middle | 800 | 2 | Fractured |
| Fractured capsules (%): | | | 22% | |

Brittle means that the capsule is not fractured in the push through test, however, the capsules might break (corresponding to the term fractured used). Fractured means that the capsule is broken.

Finding: When a hard gelatin capsule didn't break when it was packaged in blister type 1, then it was brittle. This means, that it would break easily by squeezing it manually immediately after the push through test (within less than 5 min).

Table 2.1 shows that hard gelatin capsules, that usually have a moisture content between 13-16% r.h. before packaging and which are expected to break or at least to get brittle when packaged in blister type 1, the capsule fractured percentage is 22% in 9 blisters tested.

TABLE 2.2

Blister type 1 with capsules V

| Blister | Position | Speed mm/min | Fractured —/6 | Description* |
|---|---|---|---|---|
| 1 | middle | 800 | 0 | Bent |
| 2 | middle | 800 | 0 | Bent |
| 3 | middle | 800 | 0 | Bent |
| 4 | middle | 800 | 0 | Bent |
| 5 | middle | 800 | 0 | Bent |
| 6 | middle | 800 | 0 | Bent |
| 7 | middle | 800 | 0 | Bent |
| 8 | middle | 800 | 0 | Bent |
| 9 | middle | 800 | 0 | Bent |
| Fractured capsules (%): | | | 0% | |

Bent means that the majority of capsules of blister type 1 was bent (e.g. 4/6).

TABLE 2.3

Blister type 3 with capsules V

| Blister | Position | Speed mm/min | Fractured —/6 | Description |
|---|---|---|---|---|
| 1 | middle | 800 | 0 | Bent |
| 2 | middle | 800 | 0 | Bent |
| 3 | middle | 800 | 0 | Bent |
| 4 | middle | 800 | 0 | Bent |
| 5 | middle | 800 | 0 | Bent |
| 6 | middle | 800 | 0 | Bent |
| 7 | middle | 800 | 0 | Bent |
| 8 | middle | 800 | 0 | Bent |
| 9 | middle | 800 | 0 | Bent |
| Fractured | | | 0% | |

TABLE 2.3-continued

Blister type 3 with capsules V

| Blister | Position | Speed mm/min | Fractured —/6 | Description |
|---|---|---|---|---|
| | | capsules (%): | | |

TABLE 2.4

Blister type 3 with capsules H

| Blister | Position | Speed mm/min | Fractured —/6 | Description |
|---|---|---|---|---|
| 1 | middle | 800 | 0 | — |
| 2 | middle | 800 | 0 | — |
| 3 | middle | 800 | 0 | — |
| 4 | middle | 800 | 0 | — |
| 5 | middle | 800 | 0 | — |
| 6 | middle | 800 | 0 | — |
| 7 | middle | 800 | 0 | — |
| 8 | middle | 800 | 0 | — |
| 9 | middle | 800 | 0 | — |
| | | Fractured capsules (%): | 0% | |

TABLE 2.5

Blister type 6 with capsules H

| Blister | Position | Speed mm/min | Fractured —/6 | Description |
|---|---|---|---|---|
| 1 | middle | 800 | 0 | Bent |
| 2 | middle | 800 | 0 | — |
| 3 | middle | 800 | 0 | — |
| 4 | middle | 800 | 0 | — |
| 5 | middle | 800 | 0 | — |
| 6 | middle | 800 | 1 | — |
| 7 | middle | 800 | 1 | — |
| 8 | middle | 800 | 0 | — |
| 9 | middle | 800 | 1 | — |
| | | Fractured capsules (%): | 5% | |

TABLE 2.6

Blister type 6 with capsules H when additionally stored at room temperature for one week

| Blister | Position | Speed mm/min | Fractured —/6 | Description |
|---|---|---|---|---|
| 1 | middle | 800 | 0 | Bent |
| 2 | middle | 800 | 0 | — |
| 3 | middle | 800 | 0 | — |
| 4 | middle | 800 | 0 | — |
| 5 | middle | 800 | 0 | — |
| 6 | middle | 800 | 0 | — |
| 7 | middle | 800 | 0 | — |
| 8 | middle | 800 | 0 | — |
| 9 | middle | 800 | 1 | — |
| | | Fractured capsules (%): | 2% | |

TABLE 2.7

Blister type 6 with capsules V

| Blister | Position | Speed mm/min | Fractured —/6 | Description |
|---|---|---|---|---|
| 1 | middle | 800 | 0 | Bent |
| 2 | middle | 800 | 0 | — |
| 3 | middle | 800 | 0 | — |
| 4 | middle | 800 | 0 | — |
| 5 | middle | 800 | 0 | — |
| 6 | middle | 800 | 0 | — |
| 7 | middle | 800 | 0 | — |
| 8 | middle | 800 | 0 | — |
| 9 | middle | 800 | 0 | — |
| | | Fractured capsules (%): | 0% | |

Test results after four weeks storage at 40° C. and 90% r.h.:

TABLE 3.1

Blister type 1 with capsules V

| Blister | Position | Speed mm/min | Fractured —/6 | Description |
|---|---|---|---|---|
| 1 | middle | 800 | 0 | Bent |
| 2 | middle | 800 | 0 | Bent |
| 3 | middle | 800 | 0 | Bent |
| 4 | middle | 800 | 0 | Bent |
| 5 | middle | 800 | 0 | Bent |
| 6 | middle | 800 | 0 | Bent |
| 7 | middle | 800 | 0 | Bent |
| 8 | middle | 800 | 0 | Bent |
| 9 | Middle | 800 | 0 | Bent |
| 10 | Middle | 800 | 0 | Bent |
| | | Fractured capsules (%): | 0% | |

TABLE 3.2

Blister type 1 with capsules H

| Blister | Position | Speed mm/min | Fractured —/6 | Description |
|---|---|---|---|---|
| 1 | middle | 800 | 0 | Brittle |
| 2 | middle | 800 | 1 | Fractured |
| 3 | middle | 800 | 0 | Brittle |
| 4 | middle | 800 | 1 | Fractured |
| 5 | middle | 800 | 1 | Fractured |
| 6 | middle | 800 | 1 | Fractured |
| 7 | middle | 800 | 2 | Fractured |
| 8 | middle | 800 | 2 | Fractured |
| 9 | middle | 800 | 0 | Brittle |
| 10 | middle | 800 | 2 | Fractured |
| | | Fractured capsules (%): | 17% | |

As is shown in table 3.2, 17% of hard gelatin capsules (capsules H) packaged in blister 1 having CaO as absorber material are fractured after four weeks storage time.

TABLE 3.3

Blister type 3 with capsules V

| Blister | Position | Speed mm/min | Fractured —/6 | Description |
|---|---|---|---|---|
| 1 | middle | 800 | 0 | — |
| 2 | middle | 800 | 0 | — |
| 3 | middle | 800 | 0 | — |

TABLE 3.3-continued

Blister type 3 with capsules V

| Blister | Position | Speed mm/min | Fractured —/6 | Description |
|---|---|---|---|---|
| 4 | middle | 800 | 0 | — |
| 5 | middle | 800 | 0 | — |
| 6 | middle | 800 | 0 | — |
| 7 | middle | 800 | 0 | — |
| 8 | middle | 800 | 0 | — |
| 9 | middle | 800 | 0 | — |
| 10 | middle | 800 | 0 | — |
| Fractured capsules (%): | | | 0% | |

TABLE 3.4

Blister type 3 with capsules H

| Blister | Position | Speed mm/min | Fractured —/6 | Description |
|---|---|---|---|---|
| 1 | middle | 800 | 0 | — |
| 2 | middle | 800 | 0 | — |
| 3 | middle | 800 | 0 | — |
| 4 | middle | 800 | 0 | — |
| 5 | middle | 800 | 0 | — |
| 6 | middle | 800 | 0 | — |
| 7 | middle | 800 | 0 | — |
| 8 | middle | 800 | 0 | — |
| 9 | middle | 800 | 0 | Bent |
| 10 | middle | 800 | 0 | — |
| Fractured capsules (%): | | | 0% | |

The tables with the different storage times reveal that there is no change in the results with storage time of one and four weeks, respectively.

The difference between the fracture behavior of hard gelatin capsules H packed in blister type 1 having a CaO absorber and in blister type 3 not comprising any desiccant is significant. Therefore, hard gelatin capsules (capsule H) break in blister type 1 having a CaO absorber but not in blister type 3 not comprising any desiccant. This may be due to the low relative humidity of hard gelatin capsules H packaged in blister type 1.

There is no difference between capsules V (vegetable capsules) packed in blister type 1 comprising a CaO absorber or in blister type 3 not comprising any desiccant. Both results in 0% fractured capsules V, i.e. they don't break when pushed through the lid when packed in blister type 1 which reduces the relative humidity to less than 10% r.h, or when packed in blister type 3 when packed under packaging condition of 30-50% r.h.

Further push through tests show the following results: The blisters have been stored in a climatic chamber at 40° C. and 90% r.h. for one or four weeks respectively before the push tests are performed.

TABLE 4

| | | Storage time | Number of broken capsules/12 | Fraction of broken/total number of capsules |
|---|---|---|---|---|
| Blister type 1 | Capsule H | 1 | 4 | 0.33 |
| Blister type 1 | Capsule S | 1 | 0 | 0.00 |
| Blister type 4 | Capsule H | 1 | 0 | 0.00 |
| Blister type 4 | Capsule S | 1 | 0 | 0.00 |
| Blister type 2 | Capsule H | 1 | 0 | 0.00 |
| Blister type 2 | Capsule S | 1 | 0 | 0.00 |
| Blister type 5 | Capsule H | 1 | 1 | 0.08 |
| Blister type 5 | Capsule S | 1 | 0 | 0.00 |
| Blister type 1 | Capsule H | 4 | 2 | 0.17 |
| Blister type 1 | Capsule S | 4 | 0 | 0.00 |
| Blister type 4 | Capsule H | 4 | 0 | 0.00 |
| Blister type 4 | Capsule S | 4 | 0 | 0.00 |
| Blister type 2 | Capsule H | 4 | 0 | 0.00 |
| Blister type 2 | Capsule S | 4 | 0 | 0.00 |
| Blister type 4 | Capsule H | 4 | 0 | 0.00 |
| Blister type 4 | Capsule S | 4 | 0 | 0.00 |

Above results show that the problem of fractured capsules pertains only to hard gelatin capsules that are in a too dry state, i.e. <10% r.h. Consequently, the use of a moisture-regulating buffer layer comprising KAc or any of the absorber materials of the group consisting of hygroscopic salts, silica gel or zeolite, or any mixtures thereof as absorber material and allowing to adjust the humidity in the space within the cavity surrounding the hard gelatin capsule to lie in a predefined range between 10 and 50% r.h. is superior to a blister pack having CaO as absorber or desiccant material. The results of a blister pack having a moisture-regulating buffer layer comprising KAc or any of the absorber materials of the group consisting of hygroscopic salts, silica gel or zeolite, or any mixtures thereof as humidity absorber/desiccant material is similar to a conventional blister type 3 pack not comprising any humidity absorber/desiccant material, but the latter blister pack does not allow to adjust and control the humidity of the hard gelatin capsules, so that the humidity in the cavity of the blister depends on the moisture content of the hard gelatin capsule when packed and the humidity conditions of the atmosphere when packaging the capsules. The terms humidity absorber material and desiccant material have the same meaning.

The invention will now be described by way of examples and with reference to the accompanying drawings in which.

Figure 1:
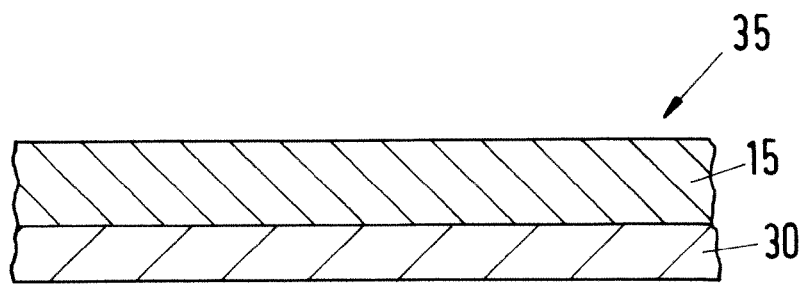
FIG. 1 shows schematically a structure of a lid film suitable for the inventive method.

FIG. 1 shows schematically a cross-section of a lid film 35 used for the inventive method. The lid film 35 comprises an outer foil 15 made of aluminium and an inner layer 30 made of polyethylene arranged on the side of the aluminium foil directed to the blister base 40, when the lid film 35 is sealed onto the blister base 40. The inner layer 30 of the lid film 35 serves as sealing layer.

Figure 2:
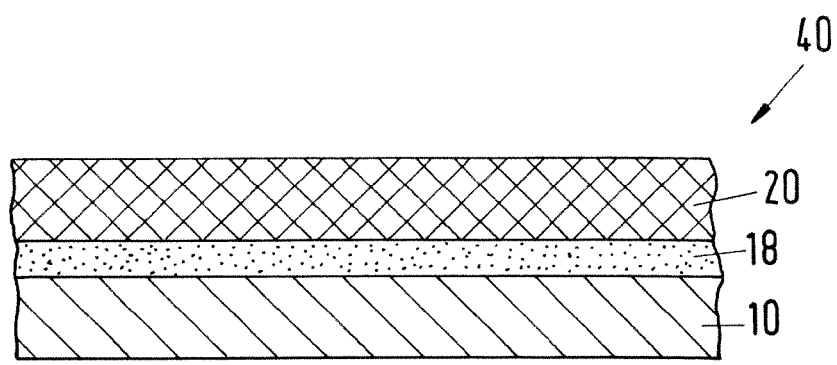
FIG. 2 shows schematically a structure of a blister base suitable for the inventive method.

FIG. 2 shows schematically a cross-section of a blister base 40 of a blister package suitable for conditioning a hard gelatin capsule filled with pharmaceuticals in order to keep the hard gelatin capsule in a dry and non-brittle state. The blister base 40 has cavities (not shown) spaced apart from one other, wherein each cavity houses a single hard gelatin capsule (not shown). The blister base 40 comprises an outer aluminium foil 10 and an inner moisture-regulating absorber layer 20 on the side of the aluminium foil 10 directed to the cavities. The moisture-regulating absorber layer 20 shown in FIG. 2 is bonded to the aluminium foil using a bonding or adhesion promoter layer 18. The bonding or adhesion promoter layer 18 is optional. The moisture-regulating absorber layer 20 contains a polymer or polymer mixture and 1 to 60 wt. % potassium acetate.

Figure 3:
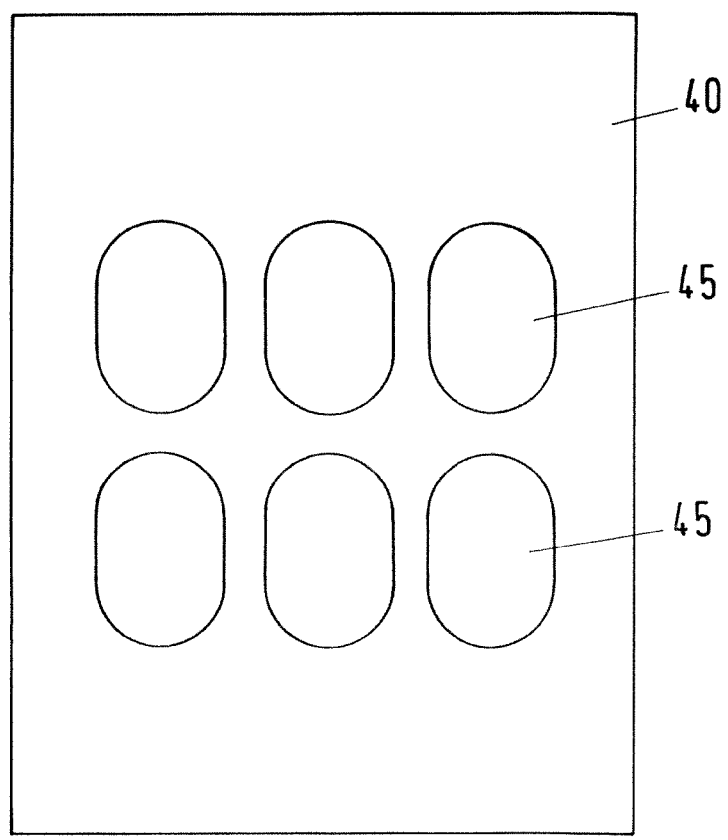
FIG. 3 shows the geometry of the blisters used for the pushing tests.

FIG. 3 shows the geometry of a blister base 40 used for the pushing tests. The blister base foil is cut into a 190×120 mm² sheet. The blister base foil 40 is inserted to the forming station, where at a forming speed of 40 cycles/min 6 cavities 45 are formed per blister. After forming the cavities 45, the blister base 40 is filled with capsules and the lid 35 is sealed at a temperature of 200° C. at a speed of 40 cycles/min. The final dimension of the lid 35 and the blister base 40 is 114×175 mm². The shape of the cavities 45 is oval in a top view and the cavities 45 have a length of 40 mm and a width of 23 mm. The distance between two adjacent cavities 45 is 7 mm in the longitudinal side and broadside.

Figure 4:
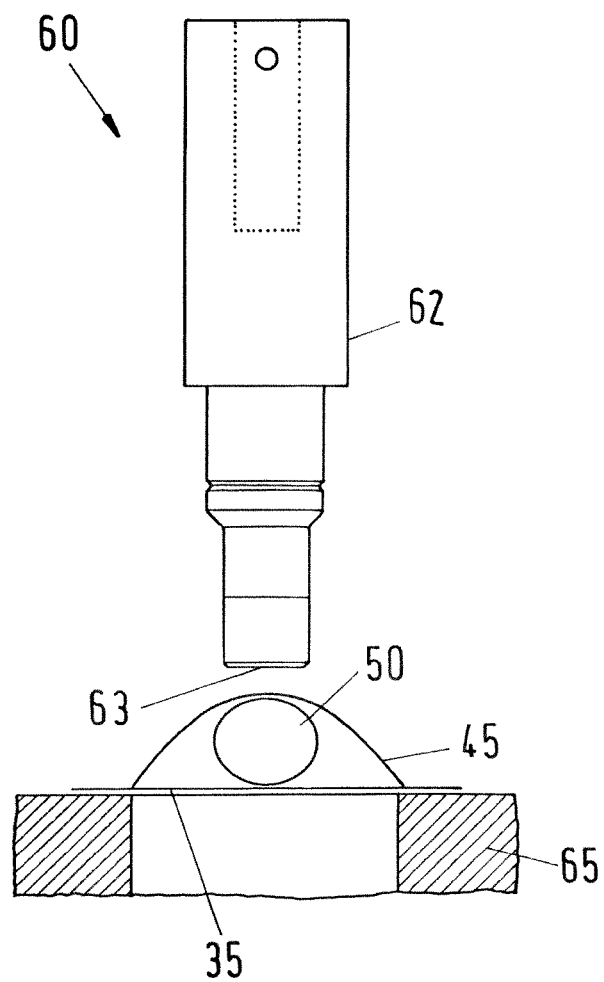
FIG. 4 shows a push through tool layout.

FIG. 4 shows the push through tool layout 60 and how the push through test is done: the upper part 62 of the tool 60 is moved downwards by a tensile tester machine spindle with a certain speed that varies between 1-800 mm/min. The bottom 63 of said upper part 62 compresses at a certain point the cavity 45 while the lid film 35 surrounding the capsule 50 is supported by the lower part 65 of the tool 60, and the capsule 50 in the cavity 45 is pushed out of the cavity 45 through the lid film 35 when the lid film 35 breaks.

Figure 5:
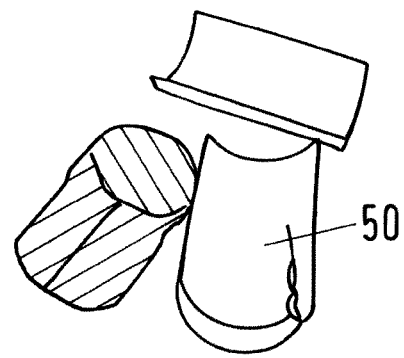
FIG. 5 shows a broken hard gelatin capsule.

FIG. 5 shows a broken hard gelatin capsule 50 after a push through test. The hard gelatin capsule 50 is of the type H and the blister where said capsule H was packed was a blister type 1.

Figure 6:
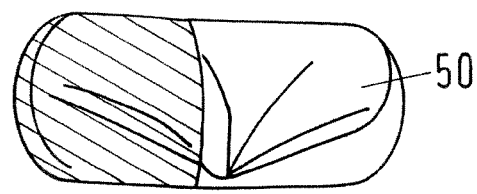
FIG. 6 shows a bent hard gelatin capsule.

FIG. 6 shows a bent hard gelatin capsule 50 of the type H after a pushing through test. The blister where said capsule H was packed was a blister type 3.

The invention claimed is:

1. A method for conditioning a hard gelatin capsule having any moisture content to a dry and non-brittle state when packed in a cavity of a blister base closed by a lid film, wherein the hard gelatin capsule is a hard starch capsule manufactured from collagen and the hard gelatin capsule contains pharmaceuticals and wherein the dry state of the hard gelatin capsule means a relative humidity of less than 50% at room temperature and the non-brittle state means that the hard gelatin capsule does not break when pressed out of the cavity of the blister base through the lid film, characterised in that the method includes the following process steps:
a) providing a lid film comprising an aluminium foil and if applicable a sealing layer made of a polyethylene and/or a moisture regulating buffer layer, further providing a blister base having at least one cavity, the lid film and/or the blister base comprising a moisture regulating buffer layer with a predefined humidity, wherein the moisture-regulating buffer layer consist of a polymer or polymer mixture containing 1 to 60 wt. % of an absorber material which is either a hygroscopic salt, a silica gel or a zeolite or a mixture of any of said absorber materials, wherein the moisture-regulating buffer layer, the lid film and/or the blister base comprising the buffer layer or a prelaminate for the lid film and/or the blister base comprising the buffer layer is exposed to a predefined moisture level, wherein the predefined moisture level of the buffer layer is such that it buffers the humidity in the space surrounding the hard gelatin capsule within the cavity closed by the lid film to lie in a range between 10 and 50% r.h.;
b) placing the hard gelatin capsule in a cavity of the blister base provided in step (a) and closing the cavity by laminating the lid film provided in step (a) to the blister base comprising the hard gelatin capsule;
c) storing the gelatin capsule for at least one week in the cavity closed by the lid film.

2. The method according to claim 1, characterised in that the moistening is done by passing the buffer layer (20), the lid film (35) and/or the blister base (40) comprising the buffer layer (20), or the prelaminate for the lid film (35) and/or the blister base (40) comprising the buffer layer (20) through a water bath, splashing it with water, or storing and/or processing it in an atmosphere having the predefined relative humidity.

3. The method according to claim 1, characterised in that the absorber material consists of potassium acetate, magnesium chloride, calcium chloride, silica gel or zeolite, or a mixture of said absorber materials.

4. The method according to claim 1, characterised in that the moisture-regulating buffer layer (20) contains 2 to 20% by weight of the absorber material.

5. The method according to claim 1, characterised in that the lid film (35) and/or the blister base (40) comprise/s an innermost sealing layer (30) directed to the cavity (45), wherein the sealing layer (30) is made of polyethylene (PE), in particular a mixture of a low density polyethylene (LDPE) and a high density polyethylene (HDPE), or another polyolefin, or modified polyolefins, or a cyclo-olefin copolymer (COC), or a ionomer.

6. The method according to claim 1, characterised in that the lid film (35) and/or the blister base (40) is/are a laminate comprising an aluminium foil (10, 15) as a moisture barrier.

7. The method according to claim 6, characterised in that the lid film (35) comprises the moisture-regulating buffer layer (20) between the aluminium foil (15) and a sealing layer (30), which is optionally bonded to the aluminium foil (15) by means of an adhesion promoter layer.

8. The method according to claim 6, characterised in that the blister base (40) comprises the aluminium foil (10) and on its inner side directed towards the cavity (45) the moisture-regulating buffer layer (20), which is optionally bonded to the aluminium foil (10) by means of an adhesion promoter layer (18).

9. The method according to claim 7, characterised in that the optional adhesion promoter layer (18) lying between the aluminium foil (10, 15) and the moisture-regulating buffer layer (20) consists of an ethylene-acrylic acid copolymer (EAA), or an ethylene-methacrylate copolymer (EMA), or a polypropylene (MAH-PP) grafted with maleic anhydride, or a polyurethane (PU) adhesive or an adhesive layer produced with solvent-containing or solvent-free adhesives.

10. The method according to claim 1, characterised in that the blister base (40) and/or the lid film (35) comprising a moisture-regulating buffer layer (20) made of polyethylene (PE), polypropylene (PP), ethylene-acrylic acid copolymer (EAA), ethylene-methacrylate copolymer (EMA), polyethylene terephthalate (PET), polyvinyl chloride (PVC) or a mixture of any of the preceding mentioned polymers is used, wherein the polymer or polymer mixture contains 1 to 60% by weight of the absorber material.

11. The method according to claim 1, characterised in that the blister base (40) comprises on its side opposite to its cavity (45) an outermost polymer film, in particular a film made of oriented polyamide (OPA).

12. The method according to claim 11, characterised in that the outermost polymer film is bonded to its adjacent layer (10) of the blister base (40) via an adhesive layer.

* * * * *